(12) United States Patent
Green et al.

(10) Patent No.: US 9,090,946 B2
(45) Date of Patent: Jul. 28, 2015

(54) SE33 MUTATIONS IMPACTING GENOTYPE CONCORDANCE

(75) Inventors: Robert Green, Cupertino, CA (US); Dennis Wang, Dublin, CA (US); Julio Mulero, Sunnyvale, CA (US); Robert Lagace, Oakland, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/239,335

(22) Filed: Sep. 21, 2011

(65) Prior Publication Data

US 2012/0070832 A1    Mar. 22, 2012

Related U.S. Application Data

(60) Provisional application No. 61/385,094, filed on Sep. 21, 2010, provisional application No. 61/466,920, filed on Mar. 23, 2011.

(51) Int. Cl.
*C12Q 1/68* (2006.01)
*C12P 19/34* (2006.01)
*C07H 21/00* (2006.01)

(52) U.S. Cl.
CPC .............. *C12Q 1/6888* (2013.01); *C12Q 1/686* (2013.01); *C12Q 2537/143* (2013.01); *C12Q 2600/156* (2013.01)

(58) Field of Classification Search
None
See application file for complete search history.

(56) References Cited

FOREIGN PATENT DOCUMENTS

WO    WO2007137320    12/2007
WO    WO2009049253    4/2009

OTHER PUBLICATIONS

Matai (Applied Biosystems, Forensic News, Jul. 2010, pp. 1-8).*
Muller et al. (Forensic Science Intl: Genetics I (2007) 205-207).*
Hering (Int J Legal Med (2002) 116:365-367).*
Sequence alignment of GenBank Accession AJ746167.1.*
Buck (Biotechniques, 1999, 27(3):528-536).*
Coticone, Sulekha R. et al., "Development of the AmpFλSTR SEfiler PCR amplification KIT: multiplex containing the highly discriminating ACTBP2 (SE33) locus", Int J Legal Med, 118: DOI 10.1007/s00414-004-0459-y, 2004, 224-234.
Heinrich, Marielle et al., "Allelic drop-out in the STR system ACTBP2 (SE33) as a result of mutations in the primer binding region", Int J Legal Med, 118: DOI 10.1007/s00414-004-0473-0, 2004, 361-363.
Hering, Sandra et al., "Sequence variations in the primer binding regions of the highly polymorphic STR system SE33", Int J Legal Med, 116: DOI 10.1007/s00414-002-0306-y, 2002, 365-367.
Hill, Carolyn R. et al., "Concordance and population studies along with stutter and peak height ratio analysis for the PowerPlex® ESX 17 and ESI 17 Systems", Forensic Science International: Genetics, 5, 2011, 269-275.
Kline, Margaret C. et al., "STR sequence analysis for characterizing normal, variant, and null alleles", Forensic Science International: Genetics, 5, 2011, 329-332.
Laszik, Andras et al., "Frequency data for the STR locus ACTBP2 (SE33) in eight populations", Int J Legal Med, 115, 2011, 94-96.
Polymeropoulos, Mihael H. et al., "Tetranucleotide repeat polymorphism at the human beta-actin related pseudogene H-beta-Ac-psi-2 (ACTBP2)", Nucleic Acids Research, vol. 20, No. 6, 1992, 1432.
Wang, Dennis Y. et al., "Identification and secondary structure analysis of a region affecting electrophoretic mobility of the STR locus SE33", Forensic Sci. Int. Genet., doi:10.1016/j.fsigen.2011.06.008, FSIGEN-765, 2011, 1-7.

* cited by examiner

*Primary Examiner* — Sarae Bausch

(57) ABSTRACT

Disclosed are primer set compositions, methods and kits for human identification using the highly complex sequence locus, SE33 (ACTBP2) in single and multiplex PCR reactions. Additionally, disclosed are three newly discovered single nucleotide polymorphisms (SNPs) within the SE33 locus that can cause discordance seen as mobility shift or allelic dropout. Also disclosed are kits useful in human identification.

6 Claims, 5 Drawing Sheets

SEQ ID NO:1

SEQ ID NO:2

FIG. 2:

SEQ ID NO:3

| | | | | | |
|---|---|---|---|---|---|
| 1 | ACAGTGAGCC | GAGGTCATGC | CATTGCACTC | CAATCTGGGC | GACAAGAGTG |
| 51 | AAACTCCGTC | AAAAGAAAGA | AAGAAAGAGA | CAAAGAGAGT | TAGAAAGAAA |
| 101 | GAAAGAGAGA | GAGAGAGAAA | GGAAGGAAGG | AAGAAAAAGA | AAGAAAAAGA |
| 151 | AAGAAAGAGA | AAGAAAGAAA | GAGAAAGAAA | GAAAGAAAGA | AAGAAAGAAA |
| 201 | GAAAGAAAGA | AAGAAAGAAA | GAAAGAAAGA | AAGAAAGAAA | GGAAAGAAAG |
| 251 | AAAGAGCAAG | TTACTATAGC | GGTAGGGGAG | ATGTTGTAGA | AATATATATA |
| 301 | AACCTCCTTA | CAC CG(C/T)(G/A)GAG ACC(G/A)CG TCAG CCC AGCGAGC |
| 341 | ACAGAACCTT | GTCCTTGCC |

FIG. 3:

| | Ethnicity | (sex) | Sample ID | SEfiler Plus | NGM SElect | Experimental | ESX17 | ESI17 | Genetic Variation |
|---|---|---|---|---|---|---|---|---|---|
| 1) | AA | (Male) | IBB039 | 17,20 | 17,20 | 17.1,20 | 17,20 | 17.1,20 | 1 |
| 2) | AA | (Male) | IBB052 | 18,20.2 | 18,20.2 | 18,20.3 | 18,20.2 | 18,20.3 | 1 |
| 3) | AA | (Fem) | IBB114 | 18,24.2 | 18,24.2 | 18,24.3 | 18,24.2 | 18,24.3 | 1 |
| 4) | AA | (Male) | IBB115 | 21,22.2 | 21,22.2 | 21,22.3 | 21,22.2 | 21,22.3 | 1 |
| 5) | AA | (Male) | IBB121 | 20,21.2 | 20,21.2 | 20,21.3 | 20,21.2 | 20,21.3 | 1 |
| 6) | AA | (Male) | IBB135 | 23.2,28.2 | 23.2,28.2 | 23.3,28.2 | 23.2,28.2 | 23.3,28.2 | 1 |
| 7) | AA | (Male) | IBB160 | 13,2,19 | 13,2,19 | 13.3,19 | 13,2,19 | 13.3,19 | 1 |
| 8) | AA | (Fem) | IBB187 | 14,21.2 | 14,21.2 | 14,21.3 | 14,21.2 | 14,21.3 | 1 |
| 9) | AA | (Fem) | IBB196 | 17,21.2 | 17,21.2 | 17,21.3 | 17,21.2 | 17,21.3 | 1 |
| 10) | AA | (Male) | IBB198 | 15,20.2 | 15,20.2 | 15,20.3 | 15,20.2 | 15,20.3 | 1 |
| 11) | AA | (Male) | IBB233 | 17,20.2 | 17,20.2 | 17,20.3 | 17,20.2 | 17,20.3 | 1 |
| 12) | AA | (Fem) | IBB253 | 20.2,21 | 20.2,21 | 20.3,21 | 20.2,21 | 20.3,21 | 1 |
| 13) | AA | (Fem) | IBB262 | 13.2,27.2 | 13.2,27.2 | 13.3,27.2 | 13.2,27.2 | 13.3,27.2 | 1 |
| 14) | AA | (Male) | IBB297 | 20.2,21 | 20.2,21 | 20.3,21 | 20.2,21 | 20.3,21 | 1 |
| 15) | AA | (Male) | IBB658 | 17,18.2 | 17,18.2 | 17,18.3 | 17,18.2 | 17,18.3 | 1 |
| 16) | AA | (Male) | IBB153 | 19,25.2 | 19,25.2 | 19,25.3 | 19,19 | 19,25.3 | 1 |
| 17) | AA | (Male) | IBB298 | 16,18 | 16,18 | 16,18.1 | 16,16 | 16,18.1 | 2 |
| 18) | C | (Fem) | IBB509 | 26.2,30.2 | 26.2,30.2 | 26.3,30.2 | 30.2,30.2 | 26.3,30.2 | 2 |
| 19) | AA | (Male) | IBB145 | 20,22.2 | 20,22.2 | 20.1,22.2 | 22.2,22.2 | 20.1,22.2 | 3 |

1 G/A$_{18}$ SNP in experimental amplicon sequence, Type 1 SNP (FIG. 1B, 5A).
2 C/T$_{10}$ SNP in experimental amplicon sequence, Type 2 SNP (FIG. 1B, 5B).
3 G/A$_{11}$ SNP in experimental amplicon sequence, Type 3 SNP (FIG. 1B, 5C).

FIG. 4:

SEQ ID NO:4
GGTAGGGGAG ATGTTGTGTAGA AATATATATA AACCTCCTTA CACCGCGGAG ACCCGCGTCAG CCCA
                                                                                                  T A           A  ← Variant SNPs
                                                                                                   2 3           1  ← SNP Type number FIG. 5A: Type 1 (IBB 39)  SEQ ID NO:5

```
CCATTGCACT CCAATCTGGG CGACAAGAGT GAAACTCCGT CAAAAGAAAG GAAACTCCGT CAAAAGAAAG ACAAAGAGAG TTAGAAAGAA
AGAAAGAGAG AGAGAGGAAG AGGAAGGAAG GAAGAGGAAG AAAGAAAAAG AAAGAAAAAG AAAGAAAGAG AGAGAAAGAA
AGAAAGAAAG AAAGAAAGAA AGAAAGAAAA AGAAAGAAAA AGAAAGAAAG AGGAAAGAAA GGAAGAGCAA
GTTACTATAG CGGTAGGGGA GATGTTGTAG AAATATATAT AAACCTCCTT ACACCGCGGA GACCACGTCA GCCCAGCGAG
C
```

FIG. 5B: Type 2 (IBB 298)  SEQ ID NO:6

```
CCATTGCACT CCAATCTGGG CGACAAGAGT GAAACTCCGT CAAAAGAAAG ACAAAGAGAG TTAGAAAGAA
AGAAAGAGAG AGAGAGGAAG AGGAAGGAAG GAAGAGGAAG AAAGAAAAAG AAAGAAAAAG AAAGAAAGAG AGAGAAAGAA
AGAAAGAAAG AAAGAAAGAA AGAAAGAAAA AGAAAGAAAA AGAAAGAAAG AGAAAGGAAG GAAAGAAAGA
GCAAGTTACT ATAGCGGTAG GGGAGATGTT GTAGAAATAT ATATAAACCT CCTTACACCG TGGAGACCGC GTCAGCCCAG
CGAGC
```

FIG. 5C: Type 3 (IBB 145)  SEQ ID NO: 7

```
CCATTGCACT CCAATCTGGG CGACAAGAGT GAAACTCCGT CAAAAGAAAG ACAAAGAGAG TTAGAAAGAA
AGAAAGAGAG AGAGAGGAAG AGGAAGGAAG GAAGAGGAAG AAAGAAAAAG AAAGAAAAAG AAAGAAAGAG AAAGAAAGAA
AGAAAGAAAG AAAGAAAGAA AGAAAGAAAA AGAAAGAAAG AGAAAGAAAA AGAAAGAAGA AAAGGAAAGA
AGAAAGAGC AAGTTACTAT AGCGGTAGGG GAGATGTTGT AGAAATATAT ATAAACCTCC TTACACCGCA GAGACCGCGT
CAGCCCAGCG AGC
```

SE33 MUTATIONS IMPACTING GENOTYPE CONCORDANCE

This application claims a priority benefit under 35 U.S.C. §119(e) from U.S. Patent Application No. 61/466,920, filed Mar. 23, 2011 and U.S. Patent Application No. 61/385,094, filed Sep. 21, 2010, which are both incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 4, 2011, is named LT0299US.txt and is 2,999 bytes in size.

FIELD

In general, the present teachings relate to the effects of three newly identified single nucleotide polymorphisms (SNPs) in the SE33 locus and their adverse impact on interpretable STR results when either a component of an amplicon or present in a primer-binding site.

BACKGROUND

The fields of forensics, paternity testing, tissue typing, and personalized medicine routinely use DNA-based techniques for identity determinations, genotyping, phenotypic prediction, and in the prediction and/or prevention of disease. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

In recent years, the discovery and development of polymorphic short tandem repeats (STRs) as genetic markers has played an important role in DNA typing. STRs have become the primary means for human identity and forensic DNA testing. In 2005, the European forensic community first published recommendations on the development of new multiplexes to provide greater discrimination power and enhanced performance on the increasing number of difficult samples encountered by forensic laboratories. Recently, the number of loci was expanded, referred to as the European Standard Set of Loci (ESSL), to include the SE33 locus for those European countries that chose to analyze this highly informative marker. The German National DNA database has included SE33 in the standard set of loci and SE33 is also profiled by neighbouring countries for data sharing purposes. SE33 is also known as ACTBP2 for β-actin pseudogene or as HUMACTBP2 and is located at 6q14. It has a high level of short tandem repeat (STR) complexity contributing to multiple length and sequence micorvariants that often create difficulties in identifying stable primer-binding sites and in primer design. With its high mutation rate and complicated short tandem repeat sequence SE33 is also highly discriminatory and useful in forensics, disaster victim identification, missing persons investigations and complex kinship analysis. Accurate DNA analysis has both identified missing persons and exonerated the innocent. The adoption of DNA test results has established DNA-based methodologies as a standard investigative, diagnostic or prognostic tool depending on the application. Matching DNA profiles produced from existing commercial STR assays with improved STR assays provides continuity and comparability of the DNA profiles within and between databases. An alteration in the DNA sequence due to, for example, an unknown mutation, polymorphism or re-arrangement, can result in allelic dropout (the failure or significantly reduced amplification of a target nucleic acid) or mobility shift (discordance of results for the same sample in relation to an allelic ladder when analyzing DNA fragment length on an electrophoresis instrument). The identification of such alterations can be useful in the continued effort to maintain the sensitivity, specificity, quality and reliability of DNA-based technologies. The occurrence of a shift in mobility or allelic dropout in new STR assays can make DNA profile matching within and between databases difficult or imprecise. Thus, careful design of new assays such that all potential amplification products are detected in as large a portion of the population as possible remains an ongoing concern when developing new STR assays. Therefore, there exists a need in the art, to improve DNA-based technologies based on the discovery of new variations in human DNA sequences.

SUMMARY

In some embodiments, a nucleic acid composition comprising a single nucleotide polymorphism (SNP) is provided. In some embodiments, the nucleic acid composition comprises a SNP located 3' of the short tandem repeat (STR) region of the SE33 locus at one of position 316, 317 or 324 as illustrated in SEQ ID NO:3. In some embodiments the SNP at position 316; wild type nucleotide is C and variant nucleotide is T, at position 317; wild type nucleotide is G and variant nucleotide is A and at position 324; wild type nucleotide is G and the variant nucleotide is A. In some embodiments, when an amplification product contains one of the variant SNPs a mobility shift is seen by capillary electrophoresis due to a destabilized of a naturally occurring hairpin between nucleotides 314 and 326.

In some embodiments, an amplification primer set for the SE33 locus is provided. In some embodiments the primer set has a first primer capable of annealing to a primer-binding site 5' of SE33's STR region and a second primer, a reverse primer, capable of annealing to a first primer-binding site 3' of the SE33 STR region, wherein the first primer-binding site comprises one variant SNP, wherein the variant SNP is selected from one of nucleotide positions 316, 317 and 324 as illustrated in SEQ ID NO:3. In some embodiments the primer set further comprising at least a third primer, a second reverse primer, capable of annealing to a second primer-binding site 3' of the SE33 STR region. In some embodiments the second, reverse primer-binding site shares 10%, 20%, 25%, 30%, 40%, 50%, 60%, 70%, 80%, 90%, 95%, 96%, 97%, 98% or 99% or more sequence identity with the first, reverse primer binding site and in other embodiments the second, reverse primer-binding site is different from the first, reverse primer binding site. In some embodiments, the 3' terminus of the second, reverse primer extends at least 1 to at least 30 nucleotides towards the 5' end of a template from the variant SNP position. In some embodiments, at least one of the reverse primers can further have a nucleotide analog or at least one universal base or at least one modified nucleotide or at least one deaza-G nucleotide or is a degenerate reverse primer.

In some embodiments, a method for amplifying a nucleic acid is provided. In some embodiments the method provides at least one forward primer capable of annealing to the SE33 locus 5' of the STR region and at least a first reverse primer capable of annealing to the SE33 locus 3' of the STR region, wherein said reverse primer anneals to at least 4 contiguous nucleotides from nucleotide positions 282 to 332 and/or nucleotide positions 351 to 359 as illustrated in SEQ ID NO:3. In some embodiments, the amplifying yields an amplification product having a variant SNP located within nucleotides 314 to 324 as illustrated in SEQ ID NO:3. In some embodiments the method further includes at least a second reverse primer, wherein said second primer can have at least one nucleotide analog or at least one universal base or can be a degenerate reverse primer wherein if present, the nucleotide analog or universal base hybridizes to a variant SNP at one of position 316, 317 or 324. In some embodiments, at least one primer in the SE33 primer set has a label and the primer set amplifies a nucleic acid sample using a polymerase chain reaction (PCR) to generate an amplification product. In some embodiments, the amplification product is detectable by capillary electrophoresis, gel electrophoresis, DNA sequencing and hybridization.

In some embodiments, a kit for analyzing a plurality of STR loci in a nucleic acid sample is disclosed. In some embodiments, the kit comprises at least an SE33 STR locus primer set, wherein the SE33 primer set generates a first amplification product for said nucleic acid sample comprising a SNP at one of position 316, 317 or 324 as illustrated in SEQ ID NO:3. In some embodiments, the SNP is a variant SNP in the first amplification product. In some embodiments, the SE33 STR locus primer set further comprises a third primer, a second reverse primer for the SE33 locus. In some embodiments, the amplification product for the SE33 primer set comprises a second amplification product resulting from the forward primer and the second, reverse primer wherein the second primer binds to a primer-binding site different than the first, reverse primer's primer-binding site. In some embodiments, the second amplification product lacks a SNP at one of position 316, 317 or 324. In some embodiments, the second amplification product includes a SNP at one of position 316, 317 or 324. In some embodiments, the SNP in the second amplification product is a variant SNP. In some embodiments, a second SE33 STR locus primer set is present in the kit or is present in a different kit. In some embodiments, the kit further has at least one SE33 control DNA, wherein the sequence of the control DNA has one variant SNP located at one of position 316, 317 or 324 as illustrated in SEQ ID NO:3. In some embodiments, the kit has at least one additional STR locus primer set selected from vWA, CSF1 PO, TPOX, D5S818, D7S820, D13S317, D16S539, D8S1179, D21S11, D18S51, TH01, FGA, D3S1358, and one or more additional STR locus primer set selected from D19S433, D2S1338, D10S1248, D22S1045, D2S441, D1S1656, CSF, D6S1043, D10S1248, Penta D, Penta E, D3S1744, D7S1517, D10S2325, D21S2055, DYS391, and D12S391. In some embodiments, the kit has a primer set for Amelogenin.

DESCRIPTION

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

BRIEF DESCRIPTION OF THE DRAWINGS

The skilled artisan will understand that the drawings described below are for illustration purposes only. The drawings are not intended to limit the scope of the present teachings in any way.

FIG. 2 illustrates an example of the SE33 locus; the STR region is indicated in bold and in larger Font, the 5' and 3' flanking regions and the disclosed SNP region (small box) with newly identified predominant/variant SNPs indicated. Large box indicates the sequences illustrated in FIG. 1A and FIG. 1B, (SEQ ID NO:3).

FIG. 3 illustrates a summary of 19 samples with discordant SE33 results.

FIG. 4 Depicts SEQ ID NO:4 and the three newly identified SNPs.

FIG. 5A-5C illustrate the DNA sequence of three discordant samples listed in FIG. 3. Each sample represents the occurrence of one of the three newly identified SNPs.

Figure 1A:
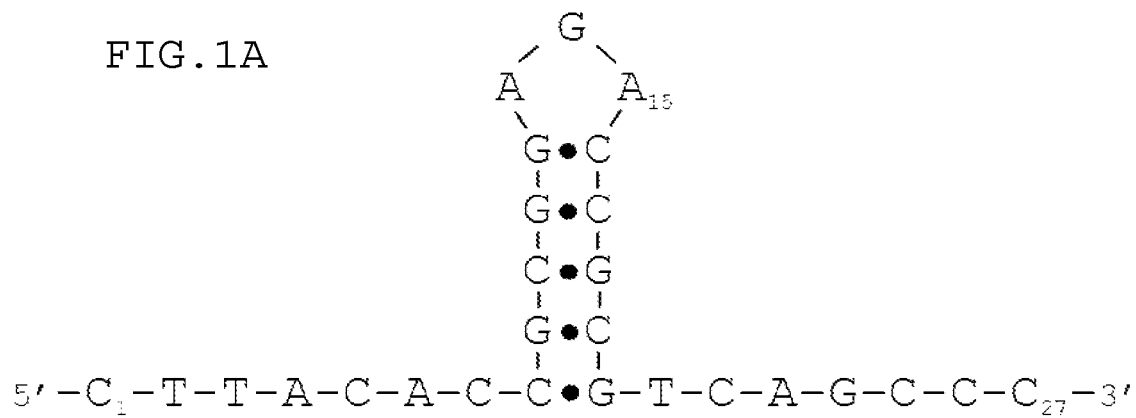
FIG. 1A-B depicts a proposed stem-loop hairpin structure containing the newly identified SNPs (SEQ ID NO:1, FIG. 1A and SEQ ID NO:2, FIG. 1B).

The practice of the teachings may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry 3$^{rd}$ Ed., W.H. Freeman Pub., New York, N.Y. and Berg et al. (2002) Biochemistry, 5$^{th}$ Ed., W.H. Freeman Pub., New York, N.Y. all of which are herein incorporated in their entirety by reference for all purposes.

The term "allelic ladder" as used herein refers to a standard size marker comprising a plurality of amplified alleles from a genetic marker.

The term "allele" as used herein refers to a genetic variation associated with a gene or a segment of DNA, i.e., one of two or more alternate forms of a DNA sequence occupying the same locus.

The term "wild type allele" or "predominant allele" are used interchangeably herein and as used herein refer to the most frequently occurring allele found in a given species, genus, family, segment, tribe, ethnicity, or racial population. The wild type allele can be considered the most common allele.

The term "variant allele" as used herein refers to a variation from the most frequently occurring allele. It can also refer to, at one or more nucleic acid positions, a change in the nucleic acid sequence at one or more positions resulting in one or more differences when compared to the most common allele at one or more nucleic acid positions as found in the allele for a given species, genus, family, segment, tribe, ethnicity, or racial population.

The term "locus" as used herein refers to a specific position on a chromosome or a nucleic acid molecule. Alleles of a locus are located at identical sites on homologous chromosomes. "Loci" is the plural of locus.

The terms "amplicon" and "amplification product" are used interchangeably and as used herein refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can comprise thermal-cycling or can be performed isothermally. In various embodiments, the term "amplification product" includes products from any number of cycles of amplification reactions.

Also herein, the recitations of numerical ranges by endpoints include all numbers subsumed within that range (e.g., 1 to 5 includes 1, 1.5, 2, 2.75, 3, 3.80, 4, 5, etc.).

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

The terms "detecting", "detected" and "detection" are used in a broad sense herein and encompass any technique by which one can determine the presence of or identify a nucleic acid sequence. In some embodiments, detecting comprises quantitating a detectable signal from the nucleic acid, including without limitation, a real-time detection method, such as quantitative PCR ("Q-PCR"). In some embodiments, detecting comprises determining the sequence of a sequencing product or a family of sequencing products generated using an amplification product as the template; in some embodiments, such detecting comprises obtaining the sequence of a family of sequencing products.

As used herein, "different" refers to separate, non-identical or distinct.

As used herein, "forward" and "reverse" are used to indicate relative orientation of primers on a polynucleotide sequence or template. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward primer is designed to anneal with the complement of the upstream primer-binding site at or near the "5'-end" of the polynucleotide in a 5' to 3' "forward" orientation, left to right. Thus, the reverse primer comprises a sequence that is complementary to the reverse or downstream primer-binding site of the polynucleotide and the forward primer comprises a sequence that is the same as the forward or upstream primer-binding site. It is to be understood that the terms "3-end" and "5'-end" as used in this paragraph are illustrative only and do not necessarily refer literally to the respective ends of the polynucleotide. Rather, the only limitation is that the reverse primer of this exemplary primer pair anneals with a reverse primer-binding site that is downstream or to the right of the forward primer-binding site that comprises the same sequence as the corresponding forward primer. As will be recognized by those of skill in the art, these terms are not intended to be limiting, but rather to provide illustrative orientation in a given embodiment.

As used herein, the terms "hybridization" and "anneal" are used interchangeably and refer to the pairing of complementary nucleic acid strands. Hybridization and the strength of hybridization (i.e., the strength of the association between nucleic acid strands) is impacted by many factors well known in the art including, but not limited to, the degree of complementarity between the nucleic acids, stringency of the conditions involved, the presence of other components (e.g., the presence or absence of polyethylene glycol), the molarity of the hybridizing strands, the G:C content of the nucleic acid strands, and so on.

As used here, the phrase "capable of binding" refers to a primer having sufficient complementary sequence composition to anneal to a target sequence at the primer-binding site.

As used herein, the term "marker" refers to the mutation in a gene which facilitates the study of its inheritance.

As used herein, the term "mobility shift" refers to the change in the expected mobility of an allele from a sample with respect to the reference allele in the allelic ladder. The mobility shift is reported as discordance of results for the same sample in relation to an allelic ladder.

As used herein, the term "gene mutation" refers to a change within a single gene giving rise to alternative genes or alleles. Gene mutations are inherited changes.

As used herein, the term "point mutation" refers to a single nucleotide base pair change in DNA. The point mutation is a gene mutation resulting from the substitution, addition, or deletion of one or a few bases (nucleobases). The point mutation can become stabilized within a genome upon replication past the altered site.

As used herein, the term "stringency" refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together. The art knows well that numerous equivalent conditions can be employed to comprise low stringency conditions.

As used herein, the terms "nucleobase" and "nucleotide" are used interchangeably and refer to a pentose (deoxyribose sugar in DNA or a ribose sugar in RNA) with a purine or pyrimidine base attached to the 1' carbon atom of the pentose and one, two or three phosphate groups attached to the 5' carbon atom of the pentose.

As used herein, the terms "polynucleotide", "oligonucleotide", and "nucleic acid" are used interchangeably and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the terms "target polynucleotide," "nucleic acid target" and "target nucleic acid" are used interchangeably and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can comprise any number of different compositional components. For example, the target can be nucleic acid (e.g. DNA or RNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, whole blood, a tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples generally, purified samples generally, and lysed cells. It will be appreciated that target polynucleotides can be isolated from samples using any of a variety of procedures known in the art, for example the PrepSEQ™ Kits (from Applied Biosystems), Boom et al., and U.S. Pat. No. 5,234,809, etc. It will be appreciated that target polynucleotides can be cut or sheared prior to analysis, including the use of such procedures as mechanical force, sonication, restriction endonuclease cleavage, or any method known in the art.

As used herein, the "polymerase chain reaction" or "PCR" is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

The term "primer" refers to a polynucleotide and analogs thereof that are capable of selectively hybridizing to a target nucleic acid or "template", a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides and the like.

As used herein, the term "amplification primer" refers to an oligonucleotide, capable of annealing to an RNA or DNA region adjacent a target sequence, and serving as an initiation primer for DNA synthesis under suitable conditions well known in the art. Typically, a PCR reaction employs a pair of amplification primers including an "upstream" or "forward" primer and a "downstream" or "reverse" primer, which delimit a region of the RNA or DNA to be amplified.

As used herein, the term "degenerate primer" refers to a primer having a mixture of nucleotides at least one position. For example, a primer can be synthesized having a G nucleotide at the 3' terminus for 50% of the primers made and an A nucleotide at the 3' terminus for the other 50% of the primers made. The difference between the two primers is the 3' terminus nucleotide where 50% are G and 50% are A.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "primer set" refers to a plurality of primers. The set can have two primers, three primers or more primers. There can be a single forward primer and a single reverse primer that together form a primer pair for a single target sequence or a multitude of primers, either alone or in pairs, triples, quadruples, etc. The primer set can be for the amplification of a plurality of target sequences, including, but not limited to, a multiplex PCR amplification reaction, for sequencing reactions and the like.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example, but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon can, but need not comprise the same sequence as or at least some of the sequence of the target flanking sequence or its complement.

Those in the art understand that as a target region is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "3' terminus" refers to the final nucleic acid at the 3' end of a polynucleotide sequence. In the example, 5' A-T-C-G 3' reading from left to right the "G" nucleotide is the 3' terminus nucleotide, the "C" nucleotide is one nucleotide from the 3' terminus, the "T" nucleotide is two nucleotides from the 3' terminus, the "A" nucleotide is three nucleotides from the 3' terminus and so on.

As used herein, the term "single nucleotide polymorphism" or SNP, refers to a variation from the most frequently occurring base at a particular nucleic acid position. A "variant SNP" refers to the variant nucleotide at a particular nucleic acid position.

As used herein, the term "short tandem repeat (STR) loci" refers to regions of the human genome which contains short, repetitive sequence elements of 3 to 7 base pairs in length. The repeats at a given STR marker or locus do not need to be perfect repeats. Examples of STRs, include but are not limited to, a triplet repeat; atcatcatc, a 4-peat; gatagata, and a 5-peat; attgc repeated 2 or more times in tandem, and so on. The STR repeat of SE33 is known as a complex repeat, for example. A complex repeat can contain numerous repeat blocks of variable unit length and also have intervening sequences of variable length.

As used herein, the term "STR region" refers to a target region that can be amplified by at least one primer annealing to a primer-binding site flanking the STR target region. For example, in a PCR reaction a first primer would anneal 5' of the STR region and a second primer would anneal 3' of the STR region. There could also be additional 5' or 3' primers depending on the characteristics, including but not limited to, the sequence complexity of the target region.

As used herein, the term "polymorphic short tandem repeat loci" refers to STR loci in which the number of repetitive sequence elements (and net length of sequence) in a particular region of genomic DNA varies from allele to allele, and from individual to individual.

As used herein, the terms "polymorphism" and "DNA polymorphism" generally refer to the condition in which two or more different nucleotide sequences in a DNA sequence coexist in the same interbreeding population.

As used herein, the terms "predominant allele", "wild type allele" and "wild type SNP" are used interchangeably and refer to the SNP most commonly found in a population.

As used herein, the term "variant allele" and "variant SNP" are used interchangeably and refer to the SNP infrequently occurring in a population.

As used herein, the term "genome" refers to the complete DNA sequence, containing the entire genetic information, of a gamete, an individual, a population, or a species.

As used herein, the term "genomic DNA" refers to the chromosomal DNA sequence of a gene or segment of a gene, including the DNA sequence of noncoding as well as coding regions. Genomic DNA also refers to DNA isolated directly from single celled organisms, cells or chromosomes or the cloned copies of all or part of such DNA.

As used herein, the term "chromosome" broadly refers to autosomes and sex chromosomes. For example, Homo sapiens contains 22 autosomes and 2 sex chromosomes, generally, either two X chromosomes or one X and one Y chromosome. The sex chromosomes determine an individual's gender. The male gender is normally imparted on an individual with a single X chromosome and a single Y chromosome whereas female gender is normally recognized when an individual has two X chromosomes. As described herein, the identification of a nucleic acid locus specific to either the X or the Y chromosome can be used to determine gender.

As used herein, the terms "gender" and "sex" refer to the two major forms of individuals of a species and can be distinguished respectively as + and − or male and female based on structures, chromosome identification and reproductive organs. The analysis of a biological sample from an individual of a species using DNA-methodologies can be used in the determination of gender based on the composition of a chromosome.

As used herein, the term "identity" refers to the identification of the gender and/or of the individual where a sample or biological sample originated.

As used herein, the term "universal base" in general refers to a base that can bind to two or more different nucleotide bases present in genomic DNA, without any substantial discrimination, for example a base that can combine with two bases is universal. Examples of universal bases include, but are not limited to, Inosine, Xanthosine, 3-nitropyrrole, 4-nitroindole, 5-nitroindole, 6-nitroindole, nitroimidazole, 4-nitropyrazole, 5-aminoindole, 4-nitrobenzimidazole, 4-aminobenzimidazole, phenyl C-ribonucleoside, benzimidazole, 5-fluoroindole, indole; acyclic sugar analogs, derivatives of hypoxanthine, imidazole 4,5-dicarboxamide, 3-nitroimidazole, 5-nitroindazole; aromatic analogs, benzene, naphthalene, phenanthrene, pyrene, pyrrole, difluorotoluene; isocarbostyril nucleoside derivatives, MICS, ICS; and hydrogen-bonding analogs, N8-pyrrolopyridine.

The term "universal base" refers to a base analog that forms "basepairs" with each of the natural DNA or RNA bases with sufficient affinity to provide for the desired level of hybridization affinity in the oligonucleotide primer of interest.

The term "percent sequence identity" refers to the result when comparing two optimally aligned sequences over a window of comparison of at least 18-20 positions or more, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. Determining the number of positions at which the identical nucleotides occur in both sequences to yield the number of matched positions, dividing the number of matched positions by the total number of positions in the reference sequence (i.e., the window size) and multiplying the results by 100 to yield the percentage of sequence identity.

The sequences recited in this application may be homologous (have similar identity). Nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more changes in nucleic acid sequence. Homology is generally inferred from sequence similarity between two or more nucleic acids (or sequences thereof). The precise percentage of similarity between sequences that is useful in establishing homology varies with the nucleic acid at issue, but as little as 25% sequence similarity is routinely used to establish homology. Higher levels of sequence similarity, e.g., 30%, 40%, 50%, 60%, 70%, 80%, 90%, 95%, 96%, 97%, 98% or 99% or more can also be used to establish homology. Methods for determining sequence similarity percentages (e.g., BLASTN using default parameters) are described herein and are generally available.

When comparing nucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 18 to 20 contiguous positions or more, in which a sequence may be compared to a reference sequence of the same number of contiguous positions after the two sequences are optimally aligned.

Optimal alignment of sequences for comparison, either polynucleotide or polypeptide, may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345 358; Hein J. (1990) Unified Approach to Alignment and Phylogenes pp. 626 645 Methods in Enzymology vol. 183, Academic Press, Inc., San Diego, Calif.; Higgins, D. G. and Sharp, P. M. (1989) CABIOS 5:151 153; Myers, E. W. and Muller W. (1988) CABIOS 4:11 17; Robinson, E. D. (1971) Comb. Theor 11: 105; Santou, N. Nes, M. (1987) Mol. Biol. Evol. 4:406 425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726 730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, BLASTN, FASTA, and TFASTA in the Wisconsin Genetics Software Package, Genetics Computer Group (GCG), 575 Science Dr., Madison, Wis.), or by inspection.

One example of algorithms that can be suitable for determining percent sequence identity and sequence similarity are the BLAST and BLAST 2.0 algorithms, which are described in Altschul et al. (1977) Nucl. Acids Res. 25:3389 3402 and Altschul et al. (1990) J. Mol. Biol. 215:403 410, respectively. BLAST and BLAST 2.0 can be used, for example with the parameters described herein, to determine percent sequence identity for the polynucleotides of the present teachings. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 18-20 positions or more, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleotides occur in both sequences to yield the number of matched positions, dividing the number of matched positions by the total number of positions in the reference sequence (i.e., the window size) and multiplying the results by 100 to yield the percentage of sequence identity.

Disclosed herein are various compositions, methods and kits for identification of a human utilizing the SE33 locus and its STR region. The human's identification can be determined by analysis of the nucleic acid found in a sample, including but not limited to a biological sample. A biological sample can be from a known or unknown source and the STR alleles so identified can be used to support identification of rapists, human identification, maternity, paternity, familial relationship, genotype, phenotype, tissue compatibility, genetic predisposition to disease, transmission of a genotype, and so on.

The term "within" refers to regions of polynucleotides suitable for primer annealing and can include the first position as well as the last position of the region and all nucleotides between the first and last nucleotides demarcating a polynucleotide region. SEQ ID NO:4 is an example of a region within SEQ ID NO:3 and includes all nucleotides of SEQ ID NO:3 from nucleotide 271 to nucleotide 334 as numbered in SEQ ID NO:3.

Suitable biological samples according to the present teachings include, but are not limited to, for example, hair, feces, blood, tissue, urine, saliva, cheek cells, skin, for example skin cells contained in fingerprints, bone, tooth, and semen. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample suspected of containing a nucleic acid and can comprise a cell, chromosomes isolated from a cell (e.g., a spread of metaphase chromosomes), genomic DNA, RNA, cDNA and the like. The contiguous string of nucleotides, i.e., polynucleotides, comprises an allele which is found in a gene which resides in a position, called a locus, which is within a chromosome.

In some embodiments, the present teachings identified three single nucleotide polymorphisms (SNPs) within nucleotides 271 to 334 as numbered in SEQ ID NO:3 (herein the "variant SNP region") of the SE33 gene locus at chromosome 6q14. The SNPs were discovered when comparing concordance of SE33 allele results between the SEfiler™ Plus Kit (Applied Biosystems, Foster City, Calif.) and prototype/experimental primers evaluated during the development of the NGM SElect™ PCR Amplification Kit (Applied Biosystems) indicated discordance at the SE33 locus. A population study of 1207 samples comprised of 350 African Americans, 333 Caucasians, 376 Hispanics and 148 Koreans showed that 18 African American samples and 1 Caucasian sample yielded discordant results at the SE33 locus when compared to the SEfiler Plus™ Kit. The source of the SE33 discordance was a shift of 0.84±0.09 nt (N=19) in one of the alleles in each of these samples generating an off ladder (OL) call when the sample was genotyped using GeneMapper® ID-X v1.2 software. All 19 alleles showing the shift were sequenced together with several wild type SE33 alleles to determine the difference between the two allele species. These investigations revealed a polymorphic region which, when a variant SNP occurs, affects the mobility of the amplicon on the capillary electrophoresis platform (FIG. 1B) (Wang, D. Y., Green, R. L., Lagacé, R. E., Oldroyd, N. J., Hennessy, L. K. and Mulero, J. L., (2011) "Identification and secondary structure analysis of a region affecting electrophoretic mobility of the STR locus SE33", Forensic Science. International: Genetics, in press, doi:10.1016/j.fsigen.2011.06.008).

In some embodiments, the present teachings provide primers and a primer-binding region 3' of the STR region of the SE33 locus. Each of the SNPs in the 3' primer-binding region, were found to result in mobility shift or allelic dropout depending on the position of the reverse primer. The mobility shift resulted in discordance and off ladder (OL) alleles, As seen in Table 1, the OL peaks were found predominantly in the African American population, resulting in 5.1% discordance between SEfiler Plus and the new prototype NGM SElect Kits. Each sample is self-identified by ethnicity and further population studies may indicate additional populations exhibiting similar discordance.

TABLE 1

Populations Studied

| | Total number of samples | Off ladders in prototype kit | Discordance with NGM SElect/ SEfiler Plus Kits |
|---|---|---|---|
| African Americans | 350 | 18 | 5.1% |
| Caucasians | 333 | 1 | 0.3% |
| Hispanics | 376 | 0 | 0% |
| Koreans | 148 | 0 | 0% |

Prototype SE33 primers were designed to better isolate the fragments from the other loci's fragments in a multiplex assay. The new SE33 locus was about 100 bp larger than the SE33 amplicon of the SEfiler Plus kit. Sequencing of the SE33 locus for each of the 19 samples revealed the occurrence of three previously unknown SNPs as shown in Table 2 and FIG. 1B.

TABLE 2

SNP Mutation and Frequency

| Mutation Occurrence | SNP Type I $G_{18}$ to A 15/19 | SNP Type II $C_{10}$ to T 3/19 | SNP Type III $G_{11}$ to A 1/19 |
|---|---|---|---|
| Sample # | IB 39 | IB 153 | IB 145 |
| | IB 52 | IB 298 | |
| | IB 114 | IB 509 | |
| | IB 115 | | |
| | IB 121 | | |
| | IB 135 | | |
| | IB 160 | | |
| | IB 187 | | |
| | IB 196 | | |
| | IB 198 | | |
| | IB 233 | | |
| | IB 253 | | |
| | IB 262 | | |
| | IB 297 | | |
| | IB 658 | | |

SNP Type 1 occurred 15 times and was only found in the African American population (wild type SNP=G, variant SNP=A). SNP Type 2—occurred 3 times, twice in African Americans and once in a Caucasian (wild type SNP=C, variant SNP=T). SNP Type 3 occurred 1 time, in one African American (wild type SNP=G, variant SNP=A). To illustrate, sample 18297 had SE33 alleles at 20.2 and 21.0 with the new NGM Select kit, which is in concordance with the SEfiler Plus kit. However, when IB297 was tested with the prototype SE33 primer set, the SE33 alleles were OL (20.3) and 21.0 (data not shown, presented in Wang et al.). In some embodiments, the present teachings have solved the problem of mobility shift associated with the amplification of the region containing the variant SNPs by repositioning the reverse primer to avoid amplification of the region containing the newly identified SNPs. Although not a reason for discordance, allelic dropout was also resolved.

The three SNPs identified among the 19 discordant samples each caused the shift whenever the variant SNP was present. The "experimental" primers used in the development of the NGM™ SElect Amplification Kit are indicted by the dotted-underline in FIG. 2 and when the variant SNP was within the resulting experimental NGM SElect kit's SE33 amplicon, discordance resulted when evaluated against the SEfiler Plus Kit. The occurrence of at least one SNP in a target nucleic acid of any one of the 19 samples caused either a mobility shift or allelic dropout. FIG. 3 provides a summary of the 19 discordant SE33 results due to a mobility shift observed in a comparison of results with the SEfiler Plus, NGM™SElect kits and the Experimental primer set. The discordant alleles are underlined. Sequencing of the 19 discordant samples revealed one of the three SNPs were present in each discordant sample. As disclosed, the mobility shift or allelic dropout was resolved by relocation of the SE33 reverse primer 5' (upstream) of the SNP region and concordance was maintained with the SEfiler Plus™ kit.

It is postulated that when the 3' SE33 experimental primer (reverse primer) was downstream of the newly identified SE33 SNP region or when an experimental reverse primer's primer-binding site included at least one of the three newly identified SE33 SNPs, when evaluated by capillary electrophoresis, mobility shift or allelic dropout, respectively, occurred.

The mobility shift resulted in discordance between the SEfiler Plus™ kit and the prototype NGM SElect kit.

Figure 1B:
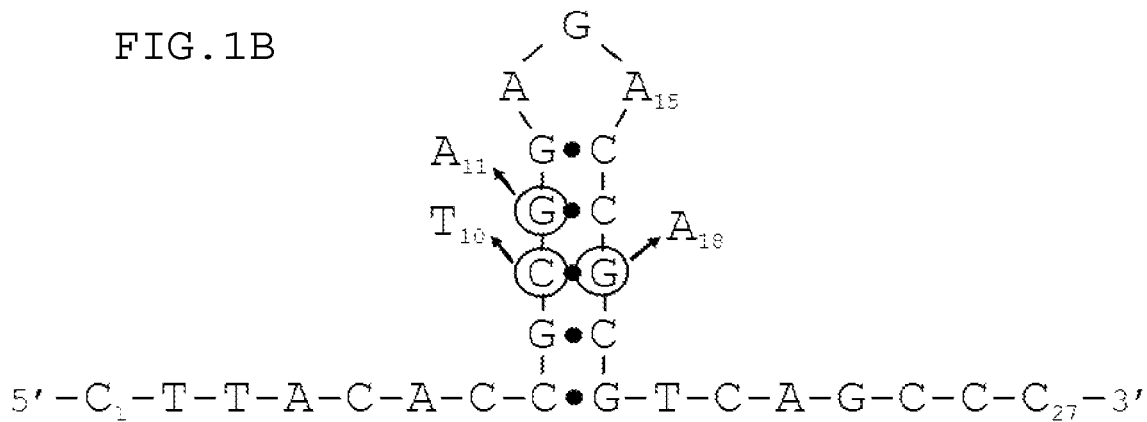

In some embodiments, the sequence surrounding the SNPs was analyzed with the DNA folding software MFOLD (M. Zucker, (1989) "On finding all suboptimal foldings of an RNA molecule", Science 244:48-52; (M. Zuker, "Mfold web server for nucleic acid folding and hybridization prediction", Nucleic Acids Res. 31 (13), 3406-15, (2003), mfold.bioinfo.rpi.edu/cgi-bin/dna-form1.cgi). MFOLD calculated the most favorable secondary structures by free energy minimization, folded the sequence into the most stable secondary structure and predicted a stem-loop (FIG. 1A). MFOLD proposed a stem-loop structure for the SE33 sequence in the region containing the three SNPs (FIG. 1A-1B). The SNPs were located within an approximately 14 nucleotide sequence region located 3', i.e., downstream, of the STR repeat region. Each of the three naturally occurring variant SNP mutations characterized in Table 2 would result in the disruption of the G-C base pairing in this stem-loop (FIG. 1B) structure. The theoretical secondary structure was tested in site-directed mutagenesis studies and then a comparison of the electrophoretic mobility of the wild type SE33 allele amplicons against the modified SE33 variant SNP containing allele amplicon sequences was performed. The nucleotide substitutions that disrupted the theoretical G-C base pairing in the stem-loop resulted in changes in the mobility of the fragment. The only nucleotide substitutions that did not result in a mobility shift were immediately outside the stem-loop and in the loop itself (data not shown, presented in Wang et al.).

FIG. 2 illustrates an example of the sequence of the SE33 locus (GenBank Accession No. AJ746167, SEQ ID NO:3), including the repeat region (larger Font, Bold) and 5' and 3' STR flanking regions with the predominant/variant SNPs in bold. While not being bound by any particular theory or proposal, the reasons for the mobility shift have several hypotheses. As seen in FIG. 1A, the region encompassing and immediately flanking the SNPs is particularly GC rich in the predominant form. The strong ionic interaction between the predominant SNPs, when present, may mitigate migration considerations when the amplified region is analyzed by capillary electrophoresis as seen in 1188/1207 samples genotyped. The sequence surrounding the SNPs could form a stem-loop structure in-silico. When a variant SNP is present, it could interrupt the stronger G-C interaction. The disruption of the secondary structure in the presence of a variant SNP could result in the shift in mobility of the SE33 allele that is detected by capillary electrophoresis. Too, if a primer, at or near the 3' terminus fails to anneal due to the presence of a variant SNP in the primer-binding region, allelic dropout can occur, also resulting in discordance.

Additional comparative testing and evaluation of discordance of the 19 samples was performed with the PowerPlex® ESX 17 and ESI 17 Systems both multiplex PCR amplification kits. Similarly, discordance was also seen in evaluating the same 19 discordant DNA samples with the PowerPlex® ESX 17 and ESI 17 Systems. Allelic dropout was observed with the ESX 17 kit and mobility shift was seen when using the ESI 17 kit. The Prom-ESI 17 kit also resulted in the same discordant (OL, 20.3, 21) allele as the prototype SE33 primers for IBB297 (data not shown). Overall, the PowerPlex ESI 17 and ESX 17 kits when testing the 19 discordant samples resulted in similar results to those obtained with the prototype SE33 primers/NGM Select prototype kit. The ESI 17 kit consistently showed a mobility shift with a Type 1, 2 or 3 SNP present in the affected allele. In contrast, the results suggest that a Type 1 SNP results in the correct genotype using ESX 17 but that Type 2 and 3 SNPs result in allele dropout of the affected allele. Thus, multiplexing reactions that include the SE33 locus impacts the size of the resulting SE33 amplicon for placement in the appropriate dye channel and SE33 primer position can adversely impact the resulting amplification when the previously unidentified SNPs were incorporated into the amplification product either by direct amplification or by being within a primer-binding site. The comparative data are summarized in FIG. 3. Readily apparent in reviewing FIG. 3 is that positioning of the reverse primer affects discordance. The Experimental (prototype SE33 primers (dotted-underlined and in Bold) for the NGM SElect prototype kit, Prom-ESX 17 and Prom-ESI 17 kits all have identical results, either discordance or allelic dropout (Prom-ESX 17, allelic dropout only). By repositioning the primers for SE33 in the NGM SElect kit, applicants have solved the mobility shift and achieved concordance between the SEfiler Plus™ and NGM SElect™ kits. Additionally, the use of the NGM SElect™ kit alone provides the specificity, sensitivity and accurately amplifies and determines the SE33 alleles, providing cost savings in a single amplification reaction, resulting in faster time to results. Two kits necessitate two reactions, sets of reagents, duplications of reaction setup and operator time, and longer time to results.

By comparisons of discordant samples between various multiplex PCR amplification kits having different primer sequences, discordance/concordance results can elucidate null or incorrect alleles for an individual result, potentially as a consequence of mutations within the primer-binding site. The Type 2 and Type 3 variant SNPs have been shown to create allelic dropout in the Prom-ESX 17 kit suggesting that the 3' terminus of the SE33 reverse primer in the Prom-ESX 17 kit is unable to fully anneal to the primer-binding site when either a Type 2 or Type 3 variant SNP (T in Type 2 and A in Type 3) is present, blocking amplification of the variant allele, resulting in allelic dropout.

Evaluations of concordance conducted by Promega for the PowerPlex ESI 17 and ESX 17 systems also indicated discordance at the SE33 locus. However, the explanation offered was a sequence difference outside of the primer positions attributed to a TTG deletion identified 41 base pairs downstream of the STR region. The sample in question typed the allele as 29.2 or 28.3 depending on if the ESI 17 or ESX 17 primer was used (C. R. Hill, et al., "Concordance and population studies along with stutter and peak height ratio analysis for the PowerPlex® ESX 17 and ESI 17 Systems", Forensic Sci. Int. Genet. (2011) 5(4):269-275, doi:10.1016/j.fsigen.2010.03.014). Although one explanation of discordance, the allelic dropout and discordance due to the variant SNPs had not been recognized with the PowerPlex ESI 17 and ESX 17 systems until the present teachings. Such results support the difficulty and obstacles to be overcome and considered in the design of SE33 primers for use in forensic applications including, but not limited to, human identification.

In other embodiments, disclosed are primer modifications such that when the 3' reverse primer anneals in an area of at least one of the variant SNPs, mobility shift and/or allelic dropout and so discordance and OL peak for the variant allele is avoided.

Other provided embodiments include, a third primer acting as a second reverse primer for the SE33 locus. The second reverse primer can have the nucleotide complementary to the variant SNP at the 3' terminus, one nucleotide, two nucleotides, three nucleotides or even four nucleotides or more from the 3' terminus of the reverse primer. Thus, if an individual carries the variant SNP, the third primer is capable of annealing to the variant SNP, amplification of the allele occurs and discordance, potentially seen as allele dropout or a null allele is avoided.

The sequence complexity of the SE33 locus is well documented. The SE33 locus has higher mutation rates than other STR loci used in routine forensic assays. The high rate of mutations contributes, in part, to the multiple length microvariants associated with the SE33 locus and its high discrimination power. The multiple length microvariants are illustrated in FIG. 5A-5C. It has been discovered that the high mutation rate and resulting multiple sequence variants have the potential to significantly affect the genotyping accuracy of the SE33 locus when PCR primers are incorrectly positioned. Thus, in some embodiments, repositioning of the reverse primer was found to not only eliminate the mobility shift of the discordant allele but, unexpectedly, upon sequencing of the 19 discordant samples, revealed the previously three unknown single nucleotide polymorphisms (SNPs) in the region 3' of the STR region of the SE33 locus on chromosome 6. 5.1% discordance was seen in 18/19 samples, all self-identified as African American and in 1/19 Caucasian sample. Allele peaks were interpreted when the peak was greater than or equal to 50 relative fluorescence units (RFUs) (data not shown). Therefore, contrary to the expectations of a person skilled in the art, incorrect primer position can result in discordance, diminishing assay specificity and sensitivity.

In some embodiments, the 3' terminus nucleotide, first nucleotide, second nucleotide, third nucleotide or even the fourth nucleotide or more from the 3' terminus of the reverse primer can be either the variant nucleotide (a thymidine, T or its compliment, an adenine, A, SNP Types 1 and 2, or a adenine, A or its compliment, a T, SNP Type 3), a universal base, or a modified base. As known to one of skill in the art, a universal base can bind to any nucleotide. Exemplary universal bases for use herein include, but are not limited to, Inosine, Xanthosine, 3-nitropyrrole (Bergstrom et al., Abstr. Pap. Am. Chem. Soc. 206(2):308 (1993); Nichols et al., Nature 369: 492-493; Bergstrom et al., J. Am. Chem. Soc. 117:1201-1209 (1995)), 4-nitroindole (Loakes et al., Nucleic Acids Res., 22:4039-4043 (1994)), 5-nitroindole (Loakes et al. (1994)), 6-nitroindole (Loakes et al. (1994)); nitroimidazole (Bergstrom et al., Nucleic Acids Res. 25:1935-1942 (1997)), 4-nitropyrazole (Bergstrom et al. (1997)), 5-aminoindole (Smith et al., Nucl. Nucl. 17:555-564 (1998)), 4-nitrobenzimidazole (Seela et al., Helv. Chim. Acta 79:488-498 (1996)), 4-aminobenzimidazole (Seela et al., Helv. Chim. Acta 78:833-846 (1995)), phenyl C-ribonucleoside (Millican et al., Nucleic Acids Res. 12:7435-7453 (1984); Matulic-Adamic et al., J. Org. Chem. 61:3909-3911 (1996)), benzimidazole (Loakes et al., Nucl. Nucl. 18:2685-2695 (1999); Papageorgiou et al., Helv. Chim. Acta 70:138-141 (1987)), 5-fluoroindole (Loakes et al. (1999)), indole (Girgis et al., J. Heterocycle Chem. 25:361-366 (1988)); acyclic sugar analogs (Van Aerschot et al., Nucl. Nucl. 14:1053-1056 (1995); Van Aerschot et al., Nucleic Acids Res. 23:4363-4370 (1995); Loakes et al., Nucl. Nucl. 15:1891-1904 (1996)), including derivatives of hypoxanthine, imidazole 4,5-dicarboxamide, 3-nitroimidazole, 5-nitroindazole; aromatic analogs (Guckian et al., J. Am. Chem. Soc. 118:8182-8183 (1996); Guckian et al., J. Am. Chem. Soc. 122:2213-2222 (2000)), including benzene, naphthalene, phenanthrene, pyrene, pyrrole, difluorotoluene; isocarbostyril nucleoside derivatives (Berger et al., Nucleic Acids Res. 28:2911-2914 (2000); Berger et al., Angew. Chem. Int. Ed. Engl., 39:2940-2942 (2000)), including MICS, ICS; hydrogen-bonding analogs, including N8-pyrrolopyridine (Seela et al., Nucleic Acids Res. 28:3224-3232 (2000)); and LNAs such as aryl-.beta.-C-LNA (Babu et al., Nucleosides, Nucleotides & Nucleic Acids 22:1317-1319 (2003); WO 03/020739). The universal base may include those disclosed by Loakes, Nucl. Acids Res., 29: 2437-2447 (2001); and Wu et al, JACS, 22: 7621-7632 (2000), all of which are hereby incorporated by reference herein.

A suitable universal base at or within 4 or more nucleotides of the 3' terminus of the PCR primer permits annealing of the primer and extension of the primer for both alleles of the SE33 SNP and so generation of the amplicon for which the primers are designed when the allelic variant is either present or when it is absent. As illustrated in FIG. 4, in various embodiments, the 3' primer-binding region has the three SNPs, SEQ ID NO:4, would be used as is known to one of skill in the art to design reverse SE33 amplification primer(s) having a complementary variant nucleotide present at or within four or more nucleotides of the 3' terminus position or if a universal base was substituted for the predominant "G" nucleotide (Type 1 and 3) or "C" nucleotide (Type 2) using primer designing programs known to one or ordinary skill in the art to avoid null or allelic dropout. Inclusion of the hairpin region containing the three SNPs in a resulting amplicon would appear to not eliminate the observed mobility shift of the SE33 locus when a variant SNP is present.

The annealing of the primer set to the target nucleic acid sequence of the sample is also contingent upon the primer hybridization (annealing) temperature used in the PCR amplification reaction which impacts primer-binding specificity. The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers anneal to complementary or substantially complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portion of the primers and their corresponding primer-binding sites in adapter-modified molecules and/or extension products, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or minor groove binders in the complementary portions of the primers and reporter probes can also influence hybridization conditions. Thus, the annealing conditions will depend upon the particular application. Such conditions, however, can be routinely determined by persons of ordinary skill in the art, without undue experimentation. Typically, annealing conditions are selected to allow the disclosed primers to selectively hybridize with a complementary or substantially complementary sequence in their corresponding adapter-modified molecule and/or extension product, but not hybridize to any significant degree to other sequences in the reaction. In some embodiments, lowering of the annealing temperature to facilitate annealing of the primer to the target nucleic acid within the primer-binding site can be used to overcome null or allelic dropout when a variant nucleotide is identified as the origin of the null or allelic dropout. As is known to one of skill in the art, the decrease in annealing temperature can also result in loss of sensitivity and specificity as well as create the potential for stutter, primer-dimer formation and excessive background.

In some embodiments, the primer set used to amplify the SE33 locus is composed of polynucleotide primers. The primers may comprise adenosine (A), thymidine (T), guanosine (G), and cytidine (C), as well as uracil (U). The primer may comprise at least one nucleoside analog for example, but not limited to, inosine, locked nucleic acids (LNA), non-nucleotide linkers, peptide nucleic acids (PNA), universal bases, and phosphoramidites) and nucleosides containing or conjugated to chemical moieties such as radionuclides (e.g., $^{32}P$ and $^{35}S$), fluorescent molecules, minor groove binders (MGBs), or any other nucleoside conjugates known in the art. The primer may consist of at least one nucleoside analog. The primer may consist essentially of at least one nucleoside analog. In some embodiments, a primer set can have one forward and two or more reverse primers. The reverse primers can bind to the same or different primer-binding sites or share one, two, three or more nucleotides between the two different primer-binding sites.

Generally, oligonucleotide primers can be chemically synthesized. Primer design and selection is a routine procedure in PCR optimization. One of ordinary skill in the art can easily design specific primers to amplify a target locus of interest, or obtain primer sets from the references listed herein.

As an example of primer selection, primers can be selected by the use of any of various software programs available and known in the art for developing amplification and/or multiplex systems. Exemplary programs include, Primer Express® software (Applied Biosystems, Foster City, Calif.) and Primer3 software (Rozen S, Skaletsky H (2000), "Primer3 on the WWW for general users and for biologist programmers," Krawetz S, Misener S (eds) Bioinformatics Methods and Protocols: Methods in Molecular Biology. Humana Press, Totowa, N.J., pp 365-386). In the example of the use of software programs, sequence information from the region of the locus of interest can be imported into the software. The software then uses various algorithms to select primers that best meet the user's specifications.

In other embodiments, included are primers for amplification of one or more STR loci simultaneously in a single amplification reaction in addition to the SE33 locus. Such systems simultaneously targeting several loci for analysis are called "multiplex" systems. Several such systems containing multiple STR loci and the Amelogenin, non-STR locus, have been described. See, e.g., AMPFℓSTR®SEFILER PLUS™ PCR AMPLIFICATION KIT USER'S MANUAL, (PN 4385739, Applied Biosystems), . . . , AMPFℓSTR® NGM™ PCR AMPLIFICATION KIT USER'S GUIDE, (PN 4425511, Applied Biosystems); J W Schumm et al., U.S. Pat. No. 7,008,771. See J. M. Butler, Forensic DNA Typing, Biology, Technology, and Genetics of STR Markers, $2^{nd}$ Edition, Elsevier, Burlington, (2005).

In some embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Qβ. replicase system (Lizardi et al., 1988, BioTechnology 6:1197 1202), and the techniques disclosed in WO 90/10064 and WO 91/03573.

In some embodiments, amplification methods comprise at least one cycle of amplification, for example, but not limited to temperature cycling. Examples of amplification techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), ligase detection reaction (LDR), LDR-PCR, strand displacement amplification (Walker et al., Nucleic Acids Res, 20, 1691 (1992); Walker et al., Proc. Nat'l Acad. Sci. U.S.A., 89, 392 (1992)), transcription-based amplification (Kwoh et al., Proc. Nat'l Acad. Sci. U.S.A., 86, 1173 (1989)) and restriction amplification (U.S. Pat. No. 5,102,784), self-sustained sequence replication (or "3SR") (Guatelli et al., Proc. Nat'l Acad. Sci. U.S.A., 87, 1874 (1990)), nucleic acid transcription-based amplification system (TAS), the Qβ replicase system (Lizardi et al., Biotechnology, 6, 1197 (1988)) and Rolling Circle Amplification (see Lizardi et al., Nat Genet 19:225 232 (1998)), hybridization signal amplification (HSAM), nucleic acid sequence-based amplification (NASBA) (Lewis, R., Genetic Engineering News, 12(9), 1 (1992)), the repair chain reaction (RCR) (Lewis, R., Genetic Engineering News, 12(9), 1 (1992)), boomerang DNA amplification (BDA) (Lewis, R., Genetic Engineering News, 12(9), 1 (1992), and branched-DNA methods. Any of the amplification techniques and methods disclosed herein can be used to practice the present teachings as would be understood by one of ordinary skill in the art.

As is understood by one of skill in the art, the Taq polymerase used in PCR often adds an extra (non-templated) nucleotide to the 3'-end of the PCR product as the template strand is copied. This non-template addition is most often adenosine (A) and results in a PCR product that is one base pair longer than the actual target sequence. A final incubation step can optionally be added after the temperature cycling steps in PCR to allow for completion of the addition of the 3' A to those strands that were missed by the Taq polymerase during the thermal cycling steps. Alternatively, the primer sequence may be selected so as to control the amount of non-templated adenylation, e.g., the use of 5' GTTTCTT sequences as taught in Brownstein et al. (BioTechniques, 20, 1004-1010, (1996).

In some embodiments, utilization of a recombinant DNA polymerase, including but not limited too TaqPCRx DNA Polymerase (P/N 11508-017, Invitrogen, Carlsbad, Calif.), can simplify PCR amplification of GC-rich templates when using standard dNTPs and thermocycling protocols for multiplex-PCR involving multiple primer sets. In other embodiments, the DNA polymerase can include DNA-dependent polymerases, which use DNA as a template, or RNA-dependent polymerases, such as reverse transcriptase, which use RNA as a template.

Based on sequence homology, DNA polymerases can be subdivided into seven different families: A, B, C, D, X, Y, and RT. DNA-dependent DNA polymerases fall into one of six families (A, B, C, D, X, and Y), with most falling into one of three families (A, B, and C). See, e.g., Ito et al. (1991) Nucleic Acids Res. 19:4045-4057; Braithwaite et al. (1993) Nucleic Acids Res. 21:787-802; Filee et al. (2002) J. Mol. Evol. 54:763-773; and Alba (2001) Genome Biol. 2:3002.1-3002.4. Certain DNA polymerases may be single-chain polypeptides (e.g., certain family A and B polymerases) or multi-subunit enzymes (e.g., certain family C polymerases) with one of the subunits having polymerase activity. Id. A fusion protein may comprise a DNA polymerase selected from a family A, B, C, D, X, or Y polymerase.

In other embodiments, the identification of a human is based on the amplification of the SE33 locus and other STR loci, such as the CODIS, loci, the European Standard Set of Loci (ESSL) by the polymerase chain reaction method (PCR) resulting in the generation of PCR amplicon(s) and the detection of the amplicon(s). In other embodiments, the amplification of the STR loci is based on the amplification by a method selected from the group consisting of the ligase detection reaction method, LDR-PCR, strand displacement amplification, transcription-based amplification, restriction amplification, self-sustained sequence replication, nucleic acid transcription-based amplification system, the Qβ replicase system, Rolling Circle Amplification, hybridization signal amplification, nucleic acid sequence-based amplification, the repair chain reaction, boomerang DNA amplification, and branched-DNA methods. Detection of the individual or multiplexed amplicons can be via any number of methods, including but not limited to for example, Northern blot (Thomas, P. S., "Hybridization of Denatured RNA and Small DNA Fragments Transferred to Nitrocellulose," Proc. Nat'l. Acad. Sci. USA, 77:5201-05 (1980), which is hereby incorporated by reference in its entirety), Southern blot (Southern, "Detection of Specific Sequences Among DNA Fragments Separated by Gel Electrophoresis," J. Mol. Biol., 98:503-17 (1975), which is incorporated herein by reference in its entirety), PCR, multiplex PCR (Erlich, et. al., "Recent Advances in the Polymerase Chain Reaction", Science 252:1643-51 (1991), which is incorporated herein by reference in its entirety), in-situ hybridization (Nucleic Acid Hybridization: A Practical Approach, Haimes and Higgins, Eds., Oxford:IRL Press (1988), which is hereby incorporated by reference in its entirety), in-situ PCR (Haase et al., "Amplification and Detection of Lentiviral DNA Inside Cells," Proc. Natl. Acad. Sci. USA, 87(13):4971-5 (1991), which is hereby incorporated by reference in its entirety), or other suitable hybridization assays known in the art. The amplification of the target nucleic acid and detecting may be carried out using well known sequence-specific amplification methods well-known to persons skilled in the art, and detected by methods including, but not limited to, gel electrophoresis, capillary electrophoresis array-capture, direct sequencing, and mass spectrometry.

In some embodiments of the present teachings, correcting for the mobility shift seen in SE33 alleles with a variant SNP can be resolved by increasing the oven temperature of the capillary electrophoresis instrument. The shift in mobility can be over come by using the 3500 instrument with a >61° C. oven temperature. Correct genotype separation of the SE33 alleles can be obtained with greater than 1.5 nucleotide separation as seen in the analysis of results from capillary electrophoresis instruments.

Various methods can be used to analyze the products of the amplified alleles in the mixture of amplification products obtained from the individual and multiplex reaction including, for example, detection of fluorescent labeled products, detection of radioisotope labeled products, silver staining of the amplification products, or the use of DNA intercalator dyes such as ethidium bromide (EtBr) and SYBR® Green cyanine dye to visualize double-stranded amplification products. Fluorescent labels suitable for attachment to primers for use in the present teachings are numerous, commercially available, and well-known in the art. With fluorescent analysis, at least one fluorescent labeled primer can be used for the amplification of each locus. Fluorescent detection may be desirable over radioactive methods of labeling and product detection, for example, because fluorescent detection does not require the use of radioactive materials, and thus avoids the regulatory and safety problems that accompany the use of radioactive materials. Fluorescent detection with labeled primers may also be selected over other non-radioactive methods of detection, such as silver staining and DNA intercalators, because fluorescent methods of detection generally reveal fewer amplification artifacts than do silver staining and DNA intercalators. This is due in part to the fact that only the amplified strands of DNA with labels attached thereto are detected in fluorescent detection, whereas both strands of every amplified product are stained and detected using the silver staining and intercalator methods of detection, which result in visualization of many non-specific amplification artifacts.

In some embodiments employed, fluorescent labeling of primers in a multiplex amplification reaction, generally at least two different labels, at least three different labels, at least four different labels, at least five different labels, and at least six or more than seven different labels can be used to label the two, three, four, five or at least six different primers or more primers. When a size marker is used to evaluate the products of the multiplex reaction, the primers used to prepare the size marker may be labeled with a label different from labels of the primers that amplify the loci of interest in the reaction. With the advent of automated fluorescent imaging and analysis, faster detection and analysis of multiplex amplification products can be achieved.

In some embodiments of the present teaching, a fluorophore can be used to label at least one primer of the multiplex amplification, e.g. by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward can more often be labeled.

The following are some examples of possible fluorophores well known in the art and suitable for use in the present teachings. The list is intended to be exemplary and is by no means exhaustive. Some possible fluorophores include: fluorescein (FL), which absorbs maximally at 492 nm and emits maximally at 520 nm; N,N,N',N'-tetramethyl-6-carboxyrhodamine (TAMRA™ dye), which absorbs maximally at 555 nm and emits maximally at 580 nm; 5-carboxyfluorescein (5-FAM™ dye), which absorbs maximally at 495 nm and emits maximally at 525 nm; 2',7'-dimethoxy-4',5'-dichloro-6-carboxyfluorescein (JOE™ dye), which absorbs maximally at 525 nm and emits maximally at 555 nm); 6-carboxy-X-rhodamine (ROX™ dye), which absorbs maximally at 585 nm and emits maximally at 605 nm; CY3™ dye, which absorbs maximally at 552 nm and emits maximally at 570 nm; CY5™ dye, which absorbs maximally at 643 nm and emits maximally at 667 nm; tetrachloro-fluorescein (TET™ dye), which absorbs maximally at 521 nm and emits maximally at 536 nm; and hexachloro-fluorescein (HEX™ dye), which absorbs maximally at 535 nm and emits maximally at 556 nm; NED™ dye, which absorbs maximally at 546 nm and emits maximally at 575 nm; 6-FAM™ dye, which emits maximally at approximately 520 nm; VIC® dye which emits maximally at approximately 550 nm; PET® dye which emits maximally at approximately 590 nm; LIZ® dye, which emits maximally at approximately 650 nm, and SID™, TED™ and TAZ™ dyes. See S R Coticone et al., U.S. Pat. No. 6,780,588; AMPFLSTR® IDENTIFILER® PCR AMPLIFICATION KIT USER'S MANUAL, pp. 1-3, Applied Biosystems (2001). Note that the above listed emission and/or absorption wavelengths are only examples and should be used for general guidance purposes only; actual peak wavelengths may vary for different applications and under different conditions.

Various embodiments of the present teachings may comprise a single multiplex system comprising at least four different dyes. These at least four dyes may comprise any four of the above-listed dyes, or any other four dyes capable of producing signals that can be distinguished from one another, e.g., 6-FAM™, VIC®, NED™ and PET® dyes. Other embodiments of the present teaching may comprise a single multiplex system comprising at least five different dyes. These at least five dyes may comprise any five of the above-listed dyes, or any other five dyes capable of producing signals that can be distinguished from one another, e.g., 6-FAM™, VIC®, NED™, PET® and LIZ® dyes. Other embodiments of the present teaching may comprise a single multiplex system comprising at least six different dyes. These at least six dyes may comprise any six of the above-listed dyes, or any other six dyes capable of producing signals that can be distinguished from one another, e.g., 5-FAM™, VIC®, NED™, PET®, LIZ® dyes and a sixth dye (SID™) with maximum emission at approximately 620 nm. The various embodiments of the subject method and compositions are not limited to any fixed number of dyes.

The PCR products can be analyzed on a sieving or non-sieving medium. In some embodiments of these teachings, for example, the PCR products can be analyzed by electrophoresis; e.g., capillary electrophoresis, as described in H. Wenz et al. (1998), GENOME RES. 8:69-80 (see also E. Buel et al. (1998), J. FORENSIC SCI. 43:(1), pp. 164-170)), or slab gel electrophoresis, as described in M. Christensen et al. (1999), SCAND. J. CLIN. LAB. INVEST. 59(3): 167-177, or denaturing polyacrylamide gel electrophoresis (see, e.g., J. Sambrook et al. (1989), in MOLECULAR CLONING: A LABORATORY MANUAL, SECOND EDITION, Cold Spring Harbor Laboratory Press, Cold Spring Harbor, N.Y., pp. 13.45-13.57). The separation of DNA fragments in electrophoresis is based primarily on differential fragment size. Amplification products can also be analyzed by chromatography; e.g., by size exclusion chromatography (SEC).

The size of the alleles present at each locus in the DNA sample can be determined by comparison to a size standard in electrophoresis, such as a DNA marker of known size. Markers for evaluation of a multiplex amplification containing two or more polymorphic STR loci may also comprise a locus-specific allelic ladder or a combination of allelic ladders for each of the loci being evaluated. See, e.g., C. Puers et al. (1993), AM. J. HUM. GENET. 53:953-958; C. Puers et al. (1994), GENOMICS 23:260-264. See also, U.S. Pat. Nos. 5,599,666; 5,674,686; and 5,783,406 for descriptions of some allelic ladders suitable for use in the detection of STR loci, and some methods of ladder construction disclosed therein. Following the construction of allelic ladders for individual loci, the ladders can be electrophoresed at the same time as the amplification products. Each allelic ladder co-migrates with the alleles from the corresponding locus.

The products of the multiplex reactions of the present teachings can also be evaluated using an internal lane standard; i.e., a specialized type of size marker configured to be electrophoresed, for example, in the same capillary as the amplification products. The internal lane standard can comprise a series of fragments of known length. The internal lane standard can also be labeled with a fluorescent dye, which is distinguishable from other dyes in the amplification reaction. The lane standard can be mixed with amplified sample or size standards/allelic ladders and electrophoresed with either, in order to compare migration in different lanes of gel electrophoresis or different capillaries of capillary electrophoresis. Variation in the migration of the internal lane standard can serve to indicate variation in the performance of the separation medium. Quantitation of this difference and correlation with the allelic ladders can provide for calibration of amplification product electrophoresed in different lanes or capillaries, and correction in the size determination of alleles in unknown samples.

Where fluorescent dyes are used to label amplification products, the electrophoresed and separated products can be analyzed using fluorescence detection equipment such as, for example, the ABI PRISM® 310 or the Applied Biosystems 3130xl Genetic Analyzer, or an ABI PRISM® 377 DNA Sequencer (Applied Biosystems, Foster City, Calif.); or a Hitachi FMBIO™ II Fluorescent Scanner (Hitachi Software Engineering America, Ltd., South San Francisco, Calif.). In various embodiments of the present teachings, PCR products can be analyzed by a capillary gel electrophoresis protocol in conjunction with such electrophoresis instrumentation such as the Applied Biosystems 3130xl genetic analyzer (Applied Biosystems) or the Applied Biosystems 3500xl Genetic Analyzer, and allelic analysis of the electrophoresed amplification products can be performed, for example, with GeneMapper® ID Software v3.2, from Applied Biosystems. In other embodiments, the amplification products can be separated by electrophoresis in, for example, about a 4.5%, 29:1 acrylamide:bis acrylamide, 8 M urea gel as prepared for an ABI PRISM®377 Automated Fluorescence DNA Sequencer.

Another suitable assay method, referred to as a 5'-nuclease assay, is described in U.S. Pat. No. 5,210,015; and Holland et al, 1991, Proc. Natl. Acad. Sci. USA 88:7276-7280; both, incorporated herein by reference. In the 5'-nuclease assay, labeled probes are degraded concomitant with primer extension by the 5' to 3' exonuclease activity of the DNA polymerase, e.g., Taq DNA polymerase. Detection of probe breakdown product indicates both that hybridization between probe and target DNA occurred and that the amplification reaction occurred. The method of real-time PCR utilizes the 5'-nuclease assay method and allows for the simultaneous detection and quantification of DNA in a sample at each PCR cycle. The incorporation of a fluorescently labeled reporter probe into the PCR reaction permits specific and reliable quantification of the target DNA being amplified.

An alternative method for detecting the amplification of nucleic acid by monitoring the increase in the total amount of double-stranded DNA in the reaction mixture is described in Higuchi et al., 1992, BioTechnology 10:413-417; Higuchi et al., 1993, BioTechnology 11:1026-1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence. A problem in this method is that the synthesis of non-target sequence, i.e., non-specific amplification, results in an increase in fluorescence which interferes with the measurement of the increase in fluorescence resulting from the synthesis of target sequences. Thus, the methods as disclosed herein are useful because they reduce non-specific amplification, thereby minimizing the increase in fluorescence resulting from the amplification of non-target sequences. The embodiments described herein provide sensitivity and specificity of detection.

In certain embodiments, detecting comprises an instrument, i.e., using an automated or semi-automated detecting means that can, but needs not, comprise a computer algorithm. In certain embodiments, a detecting instrument comprises or is coupled to a device for graphically displaying the intensity of an observed or measured parameter of an extension product or its surrogate on a graph, monitor, electronic screen, magnetic media, scanner print-out, or other two- or three-dimensional display and/or recording the observed or measured parameter. In certain embodiments, the detecting step is combined with or is a continuation of at least one separating step, for example, but not limited to, a capillary electrophoresis instrument comprising at least one fluorescent scanner and at least one graphing, recording, or readout component; a chromatography column coupled with an absorbance monitor or fluorescence scanner and a graph recorder; a chromatography column coupled with a mass spectrometer comprising a recording and/or a detection component; or a microarray with a data recording device such as a scanner or CCD camera. In certain embodiments, the detecting step is combined with an amplifying step, for example, but not limited to, real-time analysis such as Q-PCR.

In certain embodiments, the detecting step is combined with an amplifying step, for example, but not limited to, a melt curve determination. Exemplary means for performing a detecting step include the ABI PRISM® Genetic Analyzer instrument series, the ABI PRISM® DNA Analyzer instrument series, the ABI PRISM® Sequence Detection Systems instrument series, and the Applied Biosystems Real-Time PCR instrument series (all from Applied Biosystems); and microarrays and related software such as the Applied Biosystems microarray and Applied Biosystems 1700 Chemiluminescent Microarray Analyzer and other commercially available microarray and analysis systems available from Affymetrix, Agilent, and Amersham Biosciences, among others (see also Gerry et al., J. Mol. Biol. 292:251-62, 1999; De Bellis et al., Minerva Biotec. 14:247-52, 2002; and Stears et al., Nat. Med. 9:140-45, including supplements, 2003) or bead array platforms (Illumina, San Diego, Calif.). Exemplary software includes GeneMapper™ Software, GeneScan® Analysis Software, Genotyper® Software, and RapidFinder™ Software (all from Applied Biosystems).

Those in the art understand that the detection techniques employed are generally not limiting. Rather, a wide variety of detection means are within the scope of the disclosed methods and kits, provided that they allow the presence or absence of an amplicon to be determined.

The present teachings are also directed to kits that utilize the primer sets and methods described above. In some embodiments, a basic kit can comprise a container having one or more locus-specific primers. A kit can also optionally comprise instructions for use. A kit can also comprise other optional kit components, such as, for example, one or more of an allelic ladder directed to each of the specified loci, a sufficient quantity of enzyme for amplification, amplification buffer to facilitate the amplification, divalent cation solution to facilitate enzyme activity, dNTPs, modified dNTPs, dNTP analogs and 7-Deaza-dGTP for strand extension during amplification, loading solution for preparation of the amplified material for electrophoresis, one or more genomic DNAs as a template control(s), a size marker to insure that materials migrate as anticipated in the separation medium, and a protocol and manual to educate the user and limit error in use. The amounts of the various reagents in the kits also can be varied depending upon a number of factors, such as the optimum sensitivity of the process. It is within the scope of these teachings to provide test kits for use in manual applications or test kits for use with automated detectors or analyzers.

The reference works, patents, patent applications, scientific literature and other printed publications, that are referred to herein, are all hereby incorporated by reference in their entirety.

While the principles of the present teachings have been described in connection with specific embodiments, it should be understood clearly that these descriptions are made only by way of example and are not intended to limit the scope of the present teachings. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following embodiments and their equivalence.

EXAMPLES

The following procedures are representative of procedures that can be employed for analysis of nucleic acids.

DNA Sample Preparation

An extensive population study was performed with a set of approximately 1400 anonymous human DNA samples, obtained as whole blood from the Interstate Blood Bank, Inc. (Memphis, Tenn.) or Boca Biolistics (Coconut Creek, Fla.) and purified on an Applied Biosystems 6100 PrepStation (Applied Biosystems) according to the manufacture's protocol. Quantification of DNA samples was performed using the Quantifiler® Human DNA Quantification Kit (Applied Biosystems, Foster City, Calif.).

PCR Assay Set-Up:

Methods of the disclosed present teachings can be practiced as taught in the AmpFISTR® NGM SElect™ PCR Amplification Kit User's Guide, PN 4425511 (Applied Biosystems), incorporated herein by reference. The recommended NGM SElect PCR conditions call for 1.0 ng of human genomic DNA to be amplified in a total reaction volume of 25 µL. A PCR reaction mix is prepared based on the following calculation per reaction:

| Component | Volume per reaction |
|---|---|
| NGM Master Mix (2.5X) | 10 µL |
| NGM Primer Set (5X) | 5 µL |

An additional 3 reactions are included in the calculation to provide excess volume for the loss that occurs during reagent transfers. Again, thorough mixing by vortexing at medium speed for 10 sec. followed by briefly centrifuging to remove any liquid from the cap of the vial containing the PCR reaction mix. 15 µL of the PCR reaction mix is aliquoted into each reaction vial or well followed by addition of each sample to be analyzed into its own vial or well, up to 10 µL volume to have approximately 1.0 ng sample DNA/reaction. Samples of less than 10 µL are made up to a final 10 µL volume with Low-TE Buffer (consisting of 10 mM Tris-Cl pH 8.0 and 0.1 mM EDTA, was added as needed to bring the reaction volume up to 25 µL). Following sample addition the tubes or wells are covered and a brief centrifugation at 3000 rpm for about 30 seconds is performed to remove any air bubbles prior to amplification.

PCR Reaction Parameters

PCR reactions were set up in MicroAmp® 96-well reaction plates covered by either MicroAmp® 8-cap strips or MicroAmp® Clear Adhesive Film. The samples are amplified according to specifications found in the User Guide above. When using the GeneAmp PCR System 9700 with either 96-well silver or gold-plated silver block, select the 9600 Emulation Mode. Thermal cycling conditions are an initial incubation step at 95° C. for 11 min., 29 cycles of 94° C. for 20 sec. denaturing and 59° C. for 3 min. annealing followed by a final extension at 60° C. for 10 min. and final hold at 4° C. indefinitely. Following completion, the samples should be protected from light and stored at 2 to 8° C. if the amplified DNA will be analyzed within 2 weeks or at −15 to −20° C. if use is greater than 2 weeks.

Capillary Electrophoresis Sample Preparation and Detection

The amplified samples are analyzed by methods that resolve amplification product size and/or sequence differences as would be known to one of skill in the art. For example, capillary electrophoresis can be used following the instrument manufactures directions. Briefly, 0.34 GeneScan™ 600 LIZ™ Size Standard and 8.7 µL of Hi-Di™ Formamide are mixed for each sample to be analyzed. 9.0 µL of the Formamide/GeneScan-600 LIZ solution is dispensed into each well of a MicroAmp® Optical 96-well reaction plate to which a 1.0 µL aliquot of the PCR amplified sample or allelic ladder is added and the plate is covered. The plate is briefly centrifuged to mix the contents and collect them at the bottom of the plate. The plate is heated at 95° C. for 3 minutes to heat-denature the samples and then quenched immediately by placing on ice for 3 minutes.

Capillary Electrophoresis Methods and Analysis

Capillary electrophoresis (CE) was performed on the current Applied Biosystems instruments: the Applied Biosystems 3500 Genetic Analyzer, and the Applied Biosystems 3130xl Genetic Analyzer, using the specified G5 variable binning module as described in each instrument's User's Guide. The 3130xl parameters were: sample injection for 10 sec at 3 kV and electrophoresis at 15 kV for 1500 sec in Performance Optimized Polymer (POP-4™ polymer) with a run temperature of 60° C. as indicated in the GeneScan36vb_POP4DyeSetG5Module. The 3500 parameters were: sample injection for 24 sec at 1.2 kV and electrophoresis at 15 kV for 1210 sec in Performance Optimized Polymer (POP-4™ polymer) with a run temperature of 60° C. as indicated in the HID36_POP4xl_G5_NT3200 protocol. Variations in instrument parameters, e.g. injection conditions, were different on other CE instruments such as the 3500 or the 4-capillary 3130 Genetic Analyzers.) The data were collected using versions the Applied Biosystems Data Collection Software specific to the different instruments, such as v.3.0 for the 3130xl and 3500 Data Collection Software v1.0 that were analyzed using GeneMapper ID-X v1.2.

Following instrument set-up according to the manufacture's directions each sample is injected and analyzed by appropriate software, e.g., GeneMapper® ID Software v3.2 or GeneMapper® ID-X iv1.2 software with the standard NGM Kit analysis settings as specified in the User Guide following manufacturers directions. A peak amplitude of 50 RFU (relative fluorescence units) was used as the peak detection threshold.

We claim:

1. A method comprising:
   a. providing a forward primer capable of annealing to SE33 locus 5' of a short tandem repeat region,
   b. providing a reverse primer, the reverse primer comprising 10 or more contiguous nucleotides of the inverse complement of positions 316, 317, and 324 of SEQ ID NO: 3, wherein SEQ ID NO 3 comprises a T at position 316, A at position 317, or A at position 324,
   c. amplifying a nucleic acid with the forward and reverse primers,
   d. separating the amplification products by capillary electrophoresis,
   e. comparing the amplification product to an allelic ladder, and
   f. identifying the presence of the amplification products.

2. The method of claim 1, wherein at least one primer comprises a label.

3. The method of claim 1, wherein said amplifying comprises using a polymerase chain reaction (PCR) to generate an amplification product.

4. The method of claim 1, further comprising a second reverse primer.

5. The method of claim 1, further comprising primers for the loci D10S1248, vWA, D16S539, D2S1338, amelogenin, D8S1179, D21S11, D18S51, D22S1045, D19S433, TH01, FGA, D2S441, D3S1358, D1S1656 and D12S391.

6. The method of claim 1, thither comprising a size standard.

* * * * *

SEQUENCE LISTING

<160> NUMBER OF SEQ ID NOS: 7

<210> SEQ ID NO 1
<211> LENGTH: 27
<212> TYPE: DNA
<213> ORGANISM: Homo sapiens

<400> SEQUENCE: 1
cttacaccgc ggagaccgcg tcagccc

<210> SEQ ID NO 2
<211> LENGTH: 27
<212> TYPE: DNA
<213> ORGANISM: Homo sapiens

<400> SEQUENCE: 2
cttacaccgy rgagaccrcg tcagccc                                27

<210> SEQ ID NO 3
<211> LENGTH: 359
<212> TYPE: DNA
<213> ORGANISM: Homo sapiens

<400> SEQUENCE: 3
acagtgagcc gaggtcatgc cattgcactc caatctgggc gacaagagtg aaactccgtc    60
aaaagaaaga agaaagagaa caaagagagt tagaaagaaa gaaagagaga gagagagaaa   120
ggaaggaagg agaaaaagaa agaaaaagaa agaaagagaa agaaagaaag agaaagaaaa   180
gaaagaaaga agaaagaaaa gaaagaaaga agaaagaaaa gaaagaaaga aagaaagaaa   240
ggaaagaaag aaagagcaag ttactatagc ggtaggggag atgttgtaga aatatatata   300
aacctcctta caccgyrgag accrcgtcag cccagcgagc acagaacctt gtccttgcc    359

<210> SEQ ID NO 4
<211> LENGTH: 64
<212> TYPE: DNA
<213> ORGANISM: Homo sapiens

<400> SEQUENCE: 4
ggtaggggag atgttgtaga aatatatata aacctcctta caccgyrgag accrcgtcag    60
ccca                                                                64

<210> SEQ ID NO 5
<211> LENGTH: 321
<212> TYPE: DNA
<213> ORGANISM: Homo sapiens

<400> SEQUENCE: 5
ccattgcact ccaatctggg cgacaagagt gaaactccgt caaaagaaag aaagaaagag    60
acaaagagag ttagaaagaa agaaagagag agagagagaa aggaaggaag gaagaaaaag   120
aaagaaaaag aaagaaagag aaagaaagaa agagaaagaa agaaagaaag aaagaaagaa   180
agaaagaaag aaagaaagaa agaaagaaag aaagaaagaa aggaaagaaa ggaagagcaa   240
gttactatag cggtagggga gatgttgtag aaatatatat aaacctcctt acaccgcgga   300
gaccacgtca gcccagcgag c                                             321

<210> SEQ ID NO 6
<211> LENGTH: 325
<212> TYPE: DNA
<213> ORGANISM: Homo sapiens

<400> SEQUENCE: 6
ccattgcact ccaatctggg cgacaagagt gaaactccgt caaaagaaag aaagaaagag    60
acaaagagag ttagaaagaa agaaagagag agagagagaa aggaaggaag gaagaaaaag   120
aaagaaaaag aaagaaagag aaagaaagaa agagaaagaa agaaagaaag aaagaaagaa   180
agaaagaaag aaagaaagaa agaaagaaag aaagaaagaa agaaaggaag gaaagaaaga   240

```
gcaagttact atagcggtag gggagatgtt gtagaaatat atataaacct ccttacaccg      300
tggagaccgc gtcagcccag cgagc                                           325

<210> SEQ ID NO 7
<211> LENGTH: 333
<212> TYPE: DNA
<213> ORGANISM: Homo sapiens

<400> SEQUENCE: 7
ccattgcact ccaatctggg cgacaagagt gaaactccgt caaaagaaag aaagaaagag       60
acaaagagag ttagaaagaa agaaagagag agagagagaa aggaaggaag gaagaaaaag      120
aaagaaaaag aaagaaagag aaagaaagag aaagaaagaa agaaagaaag aaagaaagaa      180
agaaagaaag aaagaaagaa agaaagaaag aaagaaagaa agaaagaaag aaaggaaaga      240
aagaaagagc aagttactat agcggtaggg gagatgttgt agaaatatat ataaacctcc      300
ttacaccgca gagaccgcgt cagcccagcg agc                                  333
```